(12) United States Patent
Diebold et al.

(10) Patent No.: US 9,481,616 B2
(45) Date of Patent: Nov. 1, 2016

(54) CONVERSION OF BIOMASS FEEDSTOCKS INTO HYDROCARBON LIQUID TRANSPORTATION FUELS

(71) Applicant: COMMUNITY POWER CORPORATION, Englewood, CO (US)

(72) Inventors: James P. Diebold, Lakewood, CO (US); Steve Sherwood, Highlands Ranch, CO (US); Arthur W. Lilley, Finleyville, PA (US); Robb R. Walt, Aurora, CO (US)

(73) Assignee: COMMUNITY POWER CORPORATION, Englewood, CO (US)

( * ) Notice: Subject to any disclaimer, the term of this patent is extended or adjusted under 35 U.S.C. 154(b) by 393 days.

(21) Appl. No.: 14/088,803

(22) Filed: Nov. 25, 2013

(65) Prior Publication Data

US 2014/0161690 A1   Jun. 12, 2014

Related U.S. Application Data

(62) Division of application No. 12/535,451, filed on Aug. 4, 2009, now Pat. No. 8,624,069.

(60) Provisional application No. 61/087,327, filed on Aug. 8, 2008.

(51) Int. Cl.
*B01J 8/00* (2006.01)
*C07C 1/04* (2006.01)
(Continued)

(52) U.S. Cl.
CPC ............. *C07C 1/041* (2013.01); *B01J 8/22* (2013.01); *C01B 3/16* (2013.01); *C10G 2/32* (2013.01);
(Continued)

(58) Field of Classification Search
CPC .......................................... C10J 3/485
USPC ........ 48/127.7; 585/240; 422/626, 627, 633, 422/634
See application file for complete search history.

(56) References Cited

U.S. PATENT DOCUMENTS 3,985,519 A    10/1976   Kalina et al.
4,059,648 A *  11/1977   Derr ............... C10G 65/043
                                                   208/57

(Continued)

FOREIGN PATENT DOCUMENTS

WO    WO 97/33847      9/1997
WO    WO 2005/003067   1/2005

OTHER PUBLICATIONS

Office Action, mailed in related Chinese Patent Application No. 200980135794.X, dated Jan. 28, 2014.

(Continued)

*Primary Examiner* — Nina Bhat
(74) *Attorney, Agent, or Firm* — Thomas J. Campbell; Neal, Gerber & Eisenberg LLP (57) ABSTRACT

Methods for converting a carbon-containing feedstock into a fluid transportation fuel are described. The methods may include converting the carbon-containing feedstock into a producer gas comprising $H_2$, CO, $CO_2$, and $N_2$, and reacting the producer gas with a substrate catalyst to produce a combination of Fischer-Tropsch (F-T) products, the F-T products including the fluid transportation fuel. A portion of the F-T products may be catalytically cracked to produce additional amounts of the fluid transportation fuel. A portion of the F-T products may also be hydrogenated to produce additional amounts of the fluid transportation fuel. Apparatuses are also described for converting a carbon-containing feedstock into a fluid transportation fuel. The apparatuses may include a producer gas reactor, a Fischer-Tropsch reactor, a cracking reactor, and a hydrogenation reactor.

10 Claims, 6 Drawing Sheets

(51) Int. Cl.

| | |
|---|---|
| *B01J 8/22* | (2006.01) |
| *C01B 3/16* | (2006.01) |
| *C10G 2/00* | (2006.01) |
| *C10G 45/00* | (2006.01) |
| *C10G 47/16* | (2006.01) |
| *C10G 65/12* | (2006.01) |
| *C10G 69/04* | (2006.01) |
| *B01J 23/745* | (2006.01) |
| *B01J 29/40* | (2006.01) |

(52) U.S. Cl.
CPC ............ *C10G 45/00* (2013.01); *C10G 47/16* (2013.01); *C10G 65/12* (2013.01); *C10G 69/04* (2013.01); *B01J 23/745* (2013.01); *B01J 29/40* (2013.01); *C10G 2300/1014* (2013.01); *C10G 2300/1022* (2013.01); *C10G 2300/1092* (2013.01); *C10G 2400/02* (2013.01); *C10G 2400/04* (2013.01); *C10G 2400/08* (2013.01); *C10G 2400/30* (2013.01); *C10J 2300/0916* (2013.01); *C10J 2300/0956* (2013.01); *C10J 2300/1659* (2013.01); *Y02P 20/145* (2015.11); *Y02P 30/20* (2015.11)

(56) References Cited

U.S. PATENT DOCUMENTS

| | | | |
|---|---|---|---|
| 4,199,327 A | 4/1980 | Hempill et al. | |
| 4,252,736 A | 2/1981 | Haag et al. | |
| 4,452,611 A | 6/1984 | Richey | |
| 4,523,047 A * | 6/1985 | Chester | C07C 1/0485 208/950 |
| 4,645,585 A | 2/1987 | White | |
| 4,684,756 A | 8/1987 | Derr, Jr. | |
| 5,118,715 A | 6/1992 | Iglesia et al. | |
| 5,516,345 A | 5/1996 | Brown | |
| 6,596,780 B2 | 7/2003 | Jahnke et al. | |
| 6,864,398 B2 | 3/2005 | O'Rear | |
| 6,911,058 B2 | 6/2005 | Calderon et al. | |
| 7,214,720 B2 | 5/2007 | Bayle et al. | |
| 7,390,397 B2 | 6/2008 | Lamprecht et al. | |
| 7,393,876 B2 | 7/2008 | White et al. | |
| 8,063,258 B2 | 11/2011 | Bartek et al. | |
| 8,158,841 B2 | 4/2012 | Hara et al. | |
| 8,217,210 B2 | 7/2012 | Agrawal et al. | |
| 2001/0021724 A1 | 9/2001 | Arcuri | |
| 2005/0043418 A1 | 2/2005 | Agee | |
| 2005/0222278 A1 | 10/2005 | Agee | |
| 2006/0189702 A1 | 8/2006 | Tomlinson | |
| 2007/0006528 A1 | 1/2007 | Diebold et al. | |
| 2007/0010588 A1 | 1/2007 | Pearson | |
| 2007/0225382 A1 * | 9/2007 | Van Den Berg | C10J 3/485 518/702 |
| 2007/0259973 A1 | 11/2007 | Agee et al. | |
| 2008/0081844 A1 | 4/2008 | Shires et al. | |
| 2008/0115415 A1 * | 5/2008 | Agrawal | C01B 31/20 48/101 |
| 2008/0142410 A1 | 6/2008 | Cruijsberg | |
| 2008/0188576 A1 | 8/2008 | Tomlinson et al. | |
| 2009/0211442 A1 * | 8/2009 | Allam | C01B 3/36 95/96 |

OTHER PUBLICATIONS

"Fischer-Tropsch-Synthesis with Nitrogen-rich Syngas Fundamentals and Reactor Design Aspects" by A. Jess et al., Applied Catalysis A: General, vol. 186m p. 321-342 (1999).
"Fischer-Tropsch" from Fluidyne Gasification Internet Archive (http://www.fluidynenz.250X.com/_framed/250X/fluidynenz/fischer.htm) May 1, 2008.
"Theoretical Feasibility for Catalytic Property of Certain Ores" by S. Maity, Current science, vol. 80, No. 5 p. 628-629(2001).
International Search Report, mailed in related PCT Application No. US2009/052980, dated Oct. 13, 2009.
Supplementary European Search Report, mailed in related European Patent Application No. 09 80 5550.2, dated Oct. 12, 2012.
Office Action, mailed in corresponding Chinese Application No. 200980135794.X on Feb. 27, 2013, 11 pages.
"Liquefied Bio Fuels," NTS Inc., 2007, First Edition, pp. 423-430.
Office Action, mailed in related Japanese Patent Application No. 2011-522243, dated Dec. 24, 2013.

* cited by examiner

CONVERSION OF BIOMASS FEEDSTOCKS INTO HYDROCARBON LIQUID TRANSPORTATION FUELS

CROSS-REFERENCES TO RELATED APPLICATIONS

This application claims the benefit under 35 U.S.C. §121 as a divisional application of U.S. patent application Ser. No. 12/535,451, entitled "Conversion of Biomass Feedstocks into Hydrocarbon Liquid Transportation Fuels," filed Aug. 4, 2009, which in turn claims the benefit of U.S. Provisional Application No. 61/087,327, filed Aug. 8, 2008, each of which is herein incorporated by reference in its entirety for all purposes.

BACKGROUND OF THE INVENTION

Commercial Gas-to-Liquid (GTL) systems for converting natural gas to in to hydrocarbon liquid transportation fuels are often based on a multiplicity of complex refinery-based operations using oxygen-blown conversion of natural gas (or other fossil fuel-based resources) into synthesis gas (a.k.a. syngas) containing hydrogen ($H_2$) and carbon monoxide (CO). The syngas is converted into liquid hydrocarbon fuels and waxes through a series of Fischer-Tropsch Synthesis (FTS) reactions that are catalytically activated by a transition-metal based catalyst. The main FTS reaction is the conversion of hydrogen and carbon monoxide into the liquid hydrocarbon fuel and water:

[Reaction 1]

$$nCO + 2nH_2 \leftrightarrow \{CH_2\} + nH_2O$$

As Reaction 1 shows, each molecule of CO requires two molecules of $H_2$ to produce hydrocarbon products (liquid fuels and waxes) and one molecule of water ($H_2O$). In Biomass to Liquid (BTL) systems, the gasification of biomass to produce a hydrogen-deficient syngas (containing an approximately 1:1 mole ratio of $CO:H_2$) cannot sustain Reaction 1. Thus, for BTL systems, the $CO:H_2$ ratio may be adjusted through the Water-Gas-Shift (WGS) reaction to convert a portion of the water vapor and CO in the gasified biomass to additional $H_2$ with $CO_2$ as a byproduct:

[Reaction 2]

$$CO + H_2O \leftrightarrow H_2 + CO_2$$

In many BTL systems, the WGS reaction is catalyzed by an iron-based Fischer-Tropsch catalyst so that approximately one-half the CO in the gas reacts with an equal molar amount of water vapor (which may be sourced from the Reaction 1) to produce $H_2$ and CO. The remaining CO is converted to FTS products.

In most large-scale GTL and BTL systems, highly-polished syngas (containing only CO and $H_2$) is converted to heavy paraffinic FTS waxes at pressure of 250 to 400 psig. In a series of refinery-based operations, the FTS wax products are cracked and hydrogenated into gasoline and diesel-fuel products. These GTL facilities are usually very large (typically producing several thousands of barrels per day of diesel product) and demand on-site oxygen and hydrogen generation plants to support the gasification and fuel upgrading systems.

Unfortunately, large-scale GTL and BTL systems require significant investments of capital to build. They also need to receive the proper approvals from regulatory, environmental, and zoning authorities that can limit the ability to build these systems near the biomass sources they will utilize to make the FT fuels. The systems also need to be coupled to or located near fuel transportation infrastructure to deliver the FT fuels to their final destination (e.g., gas stations). Given the large investment of capital and difficult source to end use logistics that are typical for these large scale systems, there is a need for new methods and systems to generate FT fuels.

BRIEF SUMMARY OF THE INVENTION

The conventional wisdom is that a small biorefinery would have poor economics. However, a small-scale biorefinery allows the use of low, or even negative cost feedstocks at their source, thereby reducing or even eliminating transportation and distribution costs. This small-scale paradigm, in conjunction with a greatly simplified conversion process, will allow the quick establishment of small-scale biorefineries in locations where comparative fuels are expensive.

Small, modular liquid fuel generation and processing systems are described for generation of liquid FT fuels on-site. The processes and systems may include the generation of producer gas from a combination of gasified biomass and air that may converted to FT liquid fuels. The processes and systems may also include refining the initial FT products into liquid fuel products such as gasoline, diesel, and/or aviation fuel. These small-scale processes and systems are small fraction of the size and cost of conventional commercial GTL and BTL systems.

Embodiments of the invention include methods for converting a carbon-containing feedstock into a liquid transportation fuel. The methods may include converting the carbon-containing feedstock into a producer gas comprising $H_2$, CO, $CO_2$, and $N_2$, and reacting the producer gas with a substrate catalyst to produce a combination of Fischer-Tropsch (F-T) products, where the F-T products include the liquid transportation fuel. The methods may also include the step of catalytically cracking a portion of the F-T products to produce additional amounts of the liquid transportation fuel. In addition, the methods may include hydrogenating a portion of the F-T products to produce additional amounts of the liquid transportation fuel.

Embodiments of the invention also include apparatuses for converting a carbon-containing feedstock into a fluid transportation fuel. The apparatuses may include a producer gas reactor operable to convert the carbon-containing feedstock into a producer gas comprising $H_2$, CO, $CO_2$, and $N_2$. The apparatuses may also include a Fischer-Tropsch reactor fluidly coupled to the producer gas reactor, where the Fischer-Tropsch reactor is operable to convert a portion of the producer gas into a combination of Fischer-Tropsch (F-T) products, and where the F-T products include the fluid transportation fuel. The apparatuses may also include a cracking reactor fluidly coupled to the Fischer-Tropsch reactor, where the cracking reactor is operable to catalytically crack a portion of the F-T products to produce additional amounts of the fluid transportation fuel. In addition the apparatuses may include a hydrogenation reactor fluidly coupled to the cracking reactor, where the hydrogenation reactor is operable to hydrogenate a portion of the F-T products to produce additional amounts of the fluid transportation fuel.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

Methods and systems are described for converting carbon-containing feedstocks to fluid transportation fuels such as gasoline, diesel, and aviation fuel, among other transportation fuels. The carbon-containing feedstocks may include biomass (e.g., woodchips) that is gasified in the presence of air to make a producer gas that includes hydrogen ($H_2$), carbon monoxide (CO), carbon dioxide ($CO_2$), and nitrogen ($N_2$). The nitrogen is largely supplied by the air, and may account for about 50 mol. % of the producer gas.

The producer gas may be sent directly to a Fischer-Tropsch reactor without first passing through an air separation unit to eliminate the free nitrogen. It has been surprisingly discovered that the free nitrogen in the producer gas does not interfere with the functioning of the Fischer-Tropsch catalyst, and can even stabilize the production rates of the F-T products by acting as a temperature moderator. The heat capacity of the free nitrogen can also allow larger diameter F-T reactors (e.g., about 2 to about 3½ inches in diameter versus about 1 inch for convention F-T reactors) without concerns of runaway temperatures.

The Fischer-Tropsch catalyst may also be selected or treated to catalyze an in-situ water-gas-shift reaction in the producer gas. Producer gas made from biomass feedstocks typically has a $CO:H_2$ ratio of about 1:0.7, while the ratio should be closer to about 1:2 to sustain the production of F-T products. When the Fischer-Tropsch catalyst can catalyze a WGS reaction, the adjustment of the $CO:H_2$ ratio can take place at the F-T catalyzation site instead of in a physically separated WGS reactor.

The size of the present apparatuses are significantly smaller than conventional Fischer-Tropsch systems, and may be small enough for portable operations that are co-located with a biomass feedstock source (e.g., wooded area) and/or transportation fuel depot such as a garage, gas-station, marina, airport, etc. This can significantly reduce the costs and energy needed to transport the carbon feedstock to the apparatus, and the fuel made by the apparatus to the end-use transportation vehicle. Further details of embodiments of the present apparatuses and methods are given below.

Exemplary Apparatuses

Figure 1:
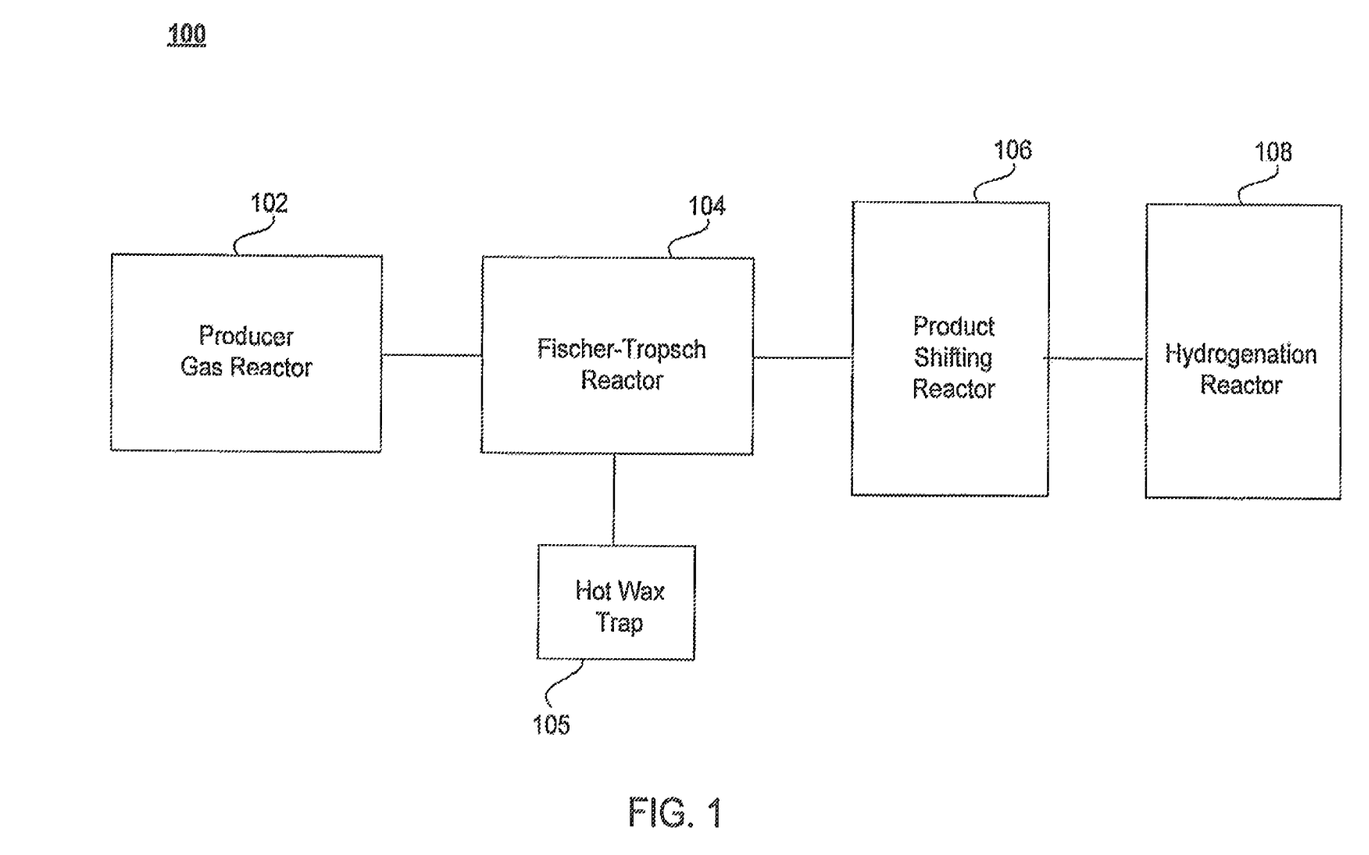
FIG. 1 is a simplified schematic showing selected components of an apparatus for converting carbon-containing feedstocks to fluid transportation fuels according to embodiments of the invention.

FIG. 1 shows a simplified schematic of selected components of an apparatus 100 for converting carbon-containing feedstocks to fluid transportation fuels according to embodiments of the invention. The apparatus 100 may include a producer gas reactor 102 that mixes a carbon-containing feedstock with air to make a producer gas. The feedstock may include gaseous, liquid or solid hydrocarbons. Examples of these hydrocarbons include coal, peat, heavy oil, light olefin hydrocarbons, natural gas, methane, ethane and/or other gaseous or liquid alkanes, alkenes, or alkynes.

The producer gas reactor 102 may also be a gasification reactor that converts carbon-containing biomass and air into producer gas. This biomass may include woody biomass, non-woody biomass, cellulosic products, cardboard, fiber board, paper, plastic, and food stuffs among other biomass. Biomass may also include human refuse that can have a negative cost as the refuse suppliers actually pay to have the refuse removed from a premises (e.g., a waste dump). Many types of biomass have low levels of sulfur and heavy metal contaminants compared to conventional hydrocarbon fuel sources like oil and coal. The moisture content of the biomass may be adjusted to about 5 wt. % to about 20 wt. % (e.g. about 15 wt. %) and placed in the gasification reactor where it is heated in the presence of air to form the producer gas.

When the feedstock is biomass, the producer gas may be a product of the pyrolysis of the biomass with molecular oxygen ($O_2$) from the supplied air. This is a controlled partial combustion process designed to partially oxidize the largest portion of the biomass into $H_2$ and CO instead of fully oxidized $H_2O$ and $CO_2$ (although both these gases are present in the producer gas). An example of a modular biomass gasification reactor that may be incorporated into embodiments of the apparatus is described in U.S. patent application Ser. No. 11/427,231 filed Jun. 28, 2006, now U.S. Pat. No. 7,909,899 issued Mar. 22, 2011, and titled "Method And Apparatus For Automated, Modular, Biomass Power Generation", the entire contents of which are herein incorporated by reference for all purposes.

The free nitrogen ($N_2$) from the air is relatively unreactive with the carbon-containing feedstock, and mostly remains as free nitrogen in the producer gas. Air is about 78 mol. % $N_2$, and the free nitrogen may account for about 50 mol. % of the producer gas. Typically, conventional F-T GTL and BTL systems separate most or all of the free nitrogen, in the producer gas using an air separation unit (ASU) and only send the purified producer gas (usually called syngas) to a F-T reactor 104. However, it has been surprisingly discovered that separating the free nitrogen is not necessary, and that the unpurified producer gas may be sent directly to the F-T reactor 104.

The F-T reactor 104 may include a substrate catalyst to convert CO and $H_2$ into F-T products as shown in Reaction 1 above. The substrate catalyst may be a transition metal and/or transition metal oxide based material such as iron and/or an iron oxide. Examples of iron-containing minerals used in the catalyst substrate include magnetite and hematite, among other minerals. The substrate catalyst may also be selected and/or treated so that it will also catalyze an in-situ water-gas-shift (WGS) reaction (see Reaction 2) to tip the ratio of $CO:H_2$ towards 1:2. For example, when the substrate catalyst is an iron-containing catalyst, it may be treated with a copper or potassium promoter that also makes it a WGS reaction catalyst. The substrate catalyst may also be exposed to a reducing atmosphere to activate F-T reaction sites on the substrate catalyst.

As noted above, when the nitrogen ($N_2$) is left in the producer gas its heat capacity may allow larger amounts of the F-T substrate catalyst to be packed into the F-T reactor 104. For example, the diameter of the tube holding the substrate catalyst may be about 2 to about 3½ inches in diameter compared to about 1 inch for conventional BTL systems. The producer gas may flow through this tube at a temperature of about 250° C. to about 300° C. The nitrogen may also allow the F-T reactor 104 to operate at lower pressure of about 250 psig or less (e.g., 150 psig) compared to conventional BTL systems which operate closer to about 300 psig.

The F-T products generated by the F-T reactor 104 may include the fluid transportation fuels such as gasoline, synthetic paraffinic kerosene (SPK), diesel fuel, and aviation fuel. The F-T products may also include smaller hydrocarbons such as methane, ethane, propanes, butanes, light olefins (e.g., ethylene, propylene and butylenes), etc., as well as larger hydrocarbons such as paraffinic waxes. These smaller and larger products may be converted into additional fluid transportation fuels by the cracking reactor 106 and the hydrogenation reactor 108.

A hot wax trap 105 may be optionally coupled to the F-T reactor 104. This trap captures hydrocarbon waxes that make up part of the F-T products. The trap 105 may be configured for the recovery of the waxes, which are also useful F-T products.

The cracking reactor 106 may catalytically crack the larger hydrocarbons (e.g., waxes) into fluid transportation fuels and may also condense unsaturated carbon-carbon bonds in, for example, light olefins to make alkyl substituted aromatic fluid transportation fuels. The cracking process may reduce the amount of larger, waxy hydrocarbon F-T products from about 20 wt. % to less than 5 wt. %.

The cracking reactor 106 may include a cracking catalyst, such as a ZSM-5 synthetic zeolite (e.g., H-ZSM-5). These zeolites are available commercially as a generic commodity product. For example, a suitable zeolite used in embodiments of the present cracking reactor 106 include H-ZSM-5 from Zeolyst International.

Some of the F-T products generated by the F-T reactor 104, as well as some of the cracked hydrocarbon products generated by the cracking reactor 106 may be hydrogenated in hydrogenation reactor 108 to produce additional fluid transportation fuels. The hydrogenation reactor 108 includes a hydrogenation catalyst that catalyzes the reaction of molecular hydrogen ($H_2$) from the producer gas with unsaturated carbon-carbon bonds in the F-T products (cracked and/or uncracked) to produce less saturated or unsaturated fluid transportation fuels. When the F-T catalyst in the F-T reactor 104 is also catalyzing a WGS reaction, enough molecular hydrogen may be generated so that no additional outside source of hydrogen is needed for the hydrogenation reactor 108.

The hydrogenation catalyst may include a palladium or platinum containing catalyst, such as 0.5% palladium on alumina. This material is commercially available from Aldrich Chemical Company (Aldrich No. 520675).

Exemplary Methods

Figure 2:
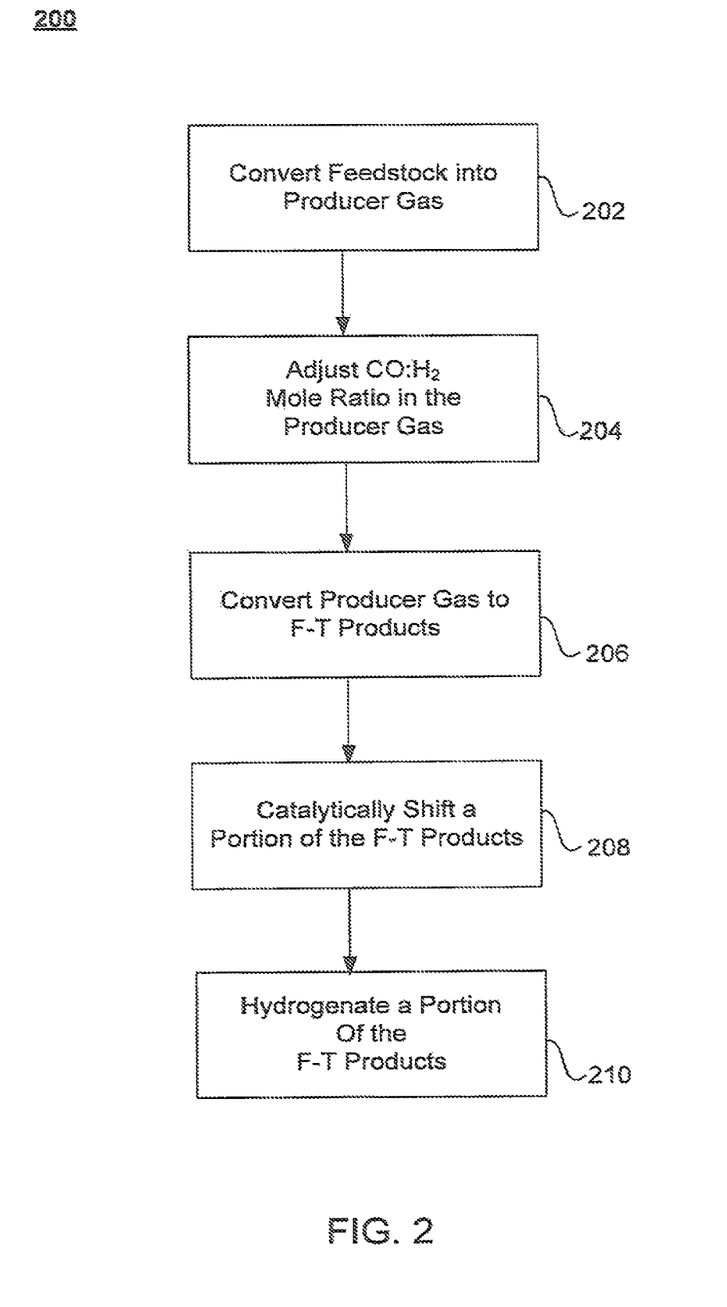
FIG. 2 is a flowchart showing selected steps in a method of converting carbon-containing feedstocks to fluid transportation fuels according to embodiments of the invention.
Figure 3A:
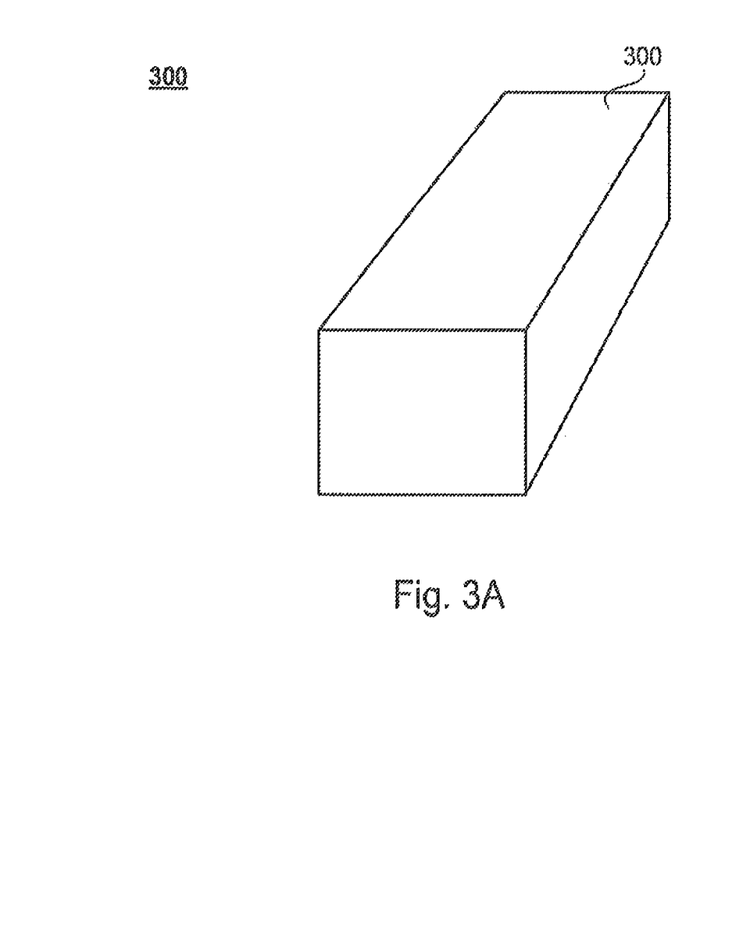
FIGS. 3A & B show simplified exemplary schematics of single and multiply coupled apparatus modules according to some embodiments of the application.
Figure 3B:
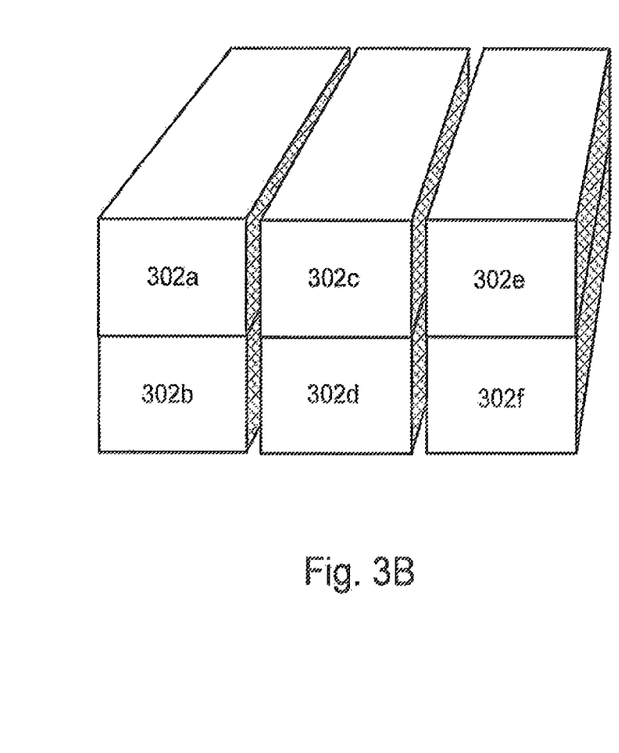
Figure 4A:
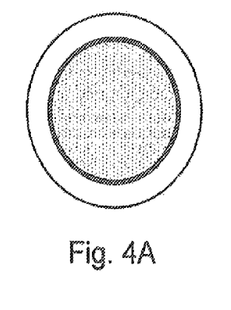
FIGS. 4A-E show examples of cross-sectional geometries of FT reactor conduits according to some embodiments of the application.
Figure 4B:
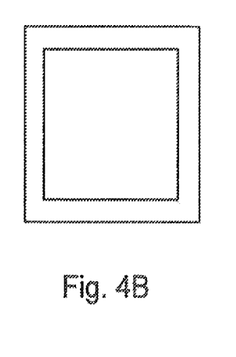
Figure 4C:
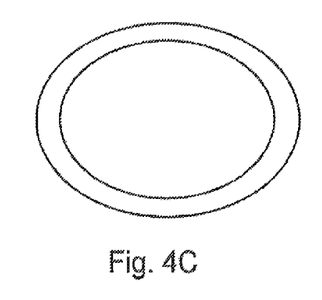
Figure 4D:
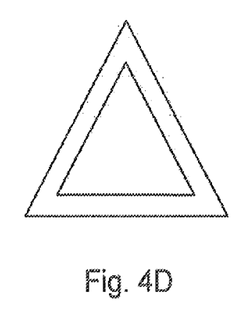
Figure 4E:
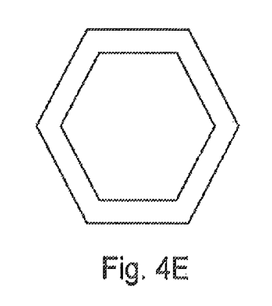
Figure 5A:
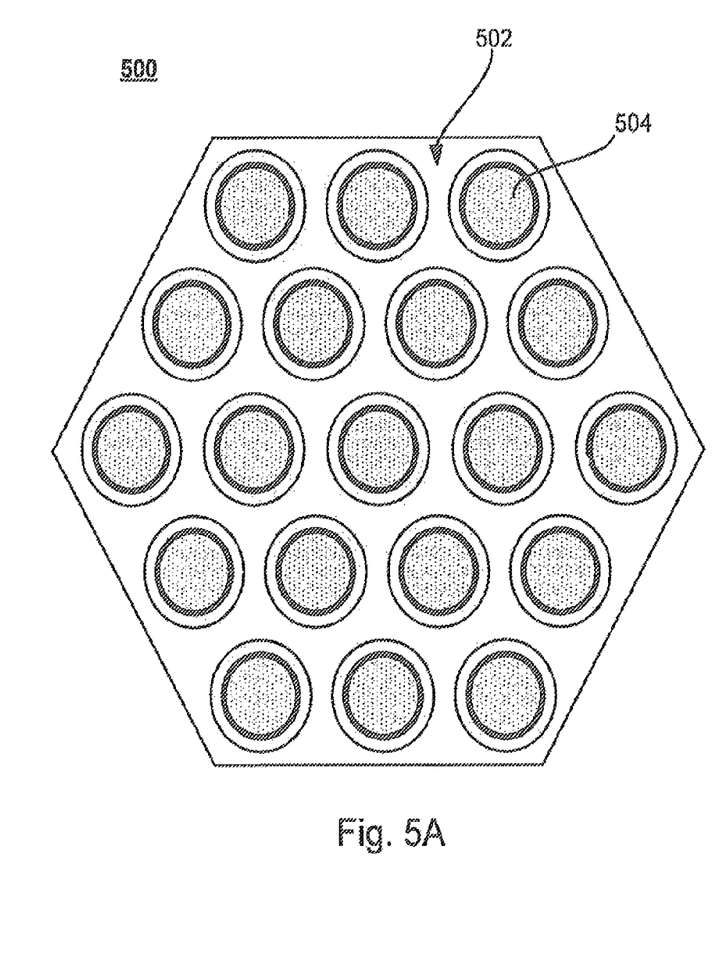
FIGS. 5A & B show examples of bundled arrangements of multiple FT reactor conduits according to some embodiments of the application.
Figure 5B:
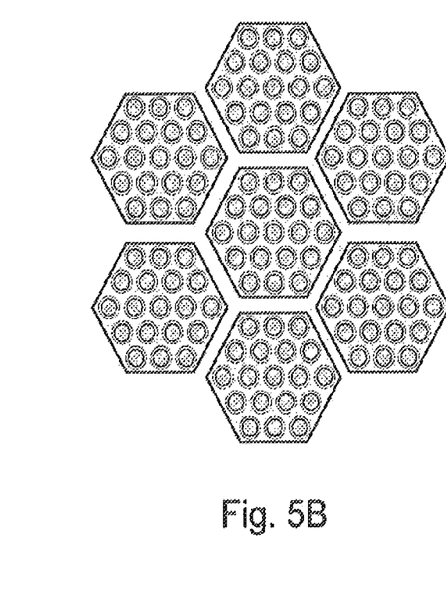
Figure 6:
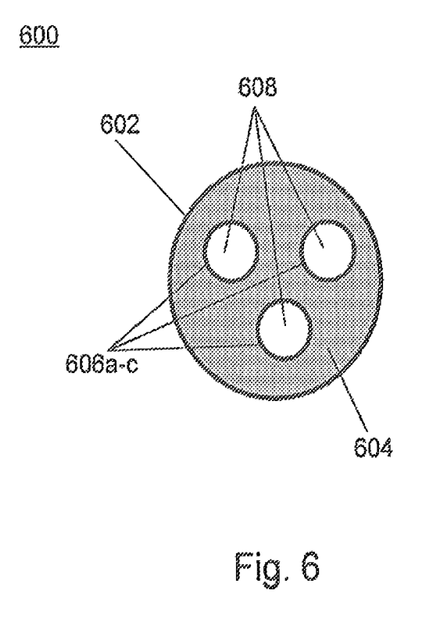
FIG. 6 shows an example of a cross-sectional FT reactor conduit that also holds cooling conduits according to some embodiments of the application.

FIG. 2 shows a flowchart with selected steps in a method 200 of converting carbon-containing feedstocks to fluid transportation fuels according to embodiments of the invention. The method 200 may include the step of converting a carbon-containing feedstock into a producer gas (202). When the feedstock is a simple alkane such as methane, a partial oxidation of the methane with air produces a syngas (i.e., $H_2$+CO) diluted in molecular nitrogen, which is the producer gas. Because the C:H ratio in methane is higher than other carbon-feedstocks like biomass, the CO:$H_2$ ratio is also higher, and may already be at the 1:2 ratio necessary for a sustained F-T reaction step (see Reaction 1).

When feedstocks like biomass are gasified into producer gas, the ratio CO:$H_2$ is about 1:0.7 and should be adjusted (204) closer to 1:2. This adjustment in the ratio may be done by a water-gas-shift (WGS) reaction in the same location as the producer gas is generated, in-situ at the site of the Fischer-Tropsch reaction, in a separate WGS reactor, or a combination of these locations.

Once the producer gas has about a 1:2 ratio of CO:$H_2$, either initially or with the help of a WGS reaction, at least a portion of the producer gas may be converted to F-T products (206) through a catalytic F-T reaction. As noted above, some of the F-T products are fluid transportation fuels that need no additional conversions or treatments. Other F-T products are too small or too large to be transportation fuels, and a portion of these products may be further converted into additional transportation fuels.

These further conversion processes may include catalytically cracking the F-T products (208). Large, waxy F-T products may be cracked into smaller fluid transportation fuels, and smaller F-T products may be cracked to form alkyl substituted aromatic components of transportation fuels. The conversion processes may also include hydrogenating some of the F-T products (210). These may include direct products from the F-T reaction, as well as catalytically cracked products that still have one or more unsaturated bonds.

The fluid transportation fuels produced by the apparatuses and methods may include room temperature liquids and gases used in transportation vehicles, including cars, trucks, boats, and airplanes, among other vehicles. The initial mixture of the fluid transportation fuels emerging from the present apparatuses may be separated into refined transportation fuels by conventional distillation and refining techniques. Because the fuels are relatively low in sulfur and other contaminants, less scrubber/purifying equipment is needed to make the final transportation fuel.

Embodiments may also include methods for converting the carbon-containing feedstock into predominantly hydrocarbon waxes instead of fluid transportation fuels. These embodiments may include bypassing the catalytic cracking and hydrogenation of the F-T products and instead recycling them through the site of the F-T reaction one or more times. The additional exposure of the F-T products to a F-T catalyst causes additional combination of smaller products into larger ones, including the hydrocarbon waxes. The heavy liquid and solid waxes may be recovered from a hot wax trap of the apparatus.

Exemplary Systems

Exemplary systems have been demonstrated to operate with compressed producer gas from the gasification of biomass. These systems were able to repeatedly shut down, temperature cycle, and restart the production of fluid FT transportation fuels with little or no loss of catalytic activity. Subsequent separation of the FT products into syngasoline and syndiesel fractions is easily accomplished by a simple distillation step.

Exemplary Fischer-Tropsch Reactor Systems

Embodiments of the FT Reactor System may include a fixed-bed biomass-to-liquid system that operates at relatively low pressures (e.g., about 170 psig to about 240 psig)

to make the F-T process more amenable to small, distributed modular applications. The FT catalyst used in the system may be made from an inexpensive iron mineral-based powdered substrate capable of doing in-situ water-gas-shift reactions as well as FTS reactions. This way the gasified biomass is not required to pass through a separate WGS reactor to adjust the mole ratio of $CO:H_2$ closer to 1:2.

The preparation of the substrate catalyst may include mixing the substrate with a blend of inorganic salt solutions to adjust the relative rate of the WGS reaction compared with the FTS reaction. The inorganic salts may also be selected to influence the quantities and types of FT products that are produced. Preparation may also include reducing the substrate with hydrogen to activate catalytic sites on the substrate's surface. In addition, a catalytic-active carbon may be deposited on the reduced substrate.

The substrate catalyst can take advantage of the 50 vol % molecular nitrogen in producer gas to increase yields of fluid FT transportation fuels. In contrast, conventional FT catalysts are designed to work with pure syngas that contains only CO and $H_2$ without the molecular nitrogen present. The substrate catalyst can convert the producer gas into a variety of FT products, including methane, ethane, propanes, butanes, light olefins (e.g., ethylene, propylene, butylenes, etc.), gasoline, synthetic paraffinic kerosene (SPK), diesel fuels, and waxes, among other products. Some of these products, such as the waxes and light olefins, may be converted into additional stable fluid fuels by cracking and/or hydrogenation. Embodiments of present reactor systems may include downstream reactors for cracking and/or hydrogenation.

Exemplary Cracking Reactor

In a downstream processing step, raw FT products may be sent through a packed bed of a zeolite cracking catalyst to convert high molecular weight waxes to room-temperature liquid fuels, and to condense light olefins to methyl and ethyl substituted aromatic gasoline and diesel constituents. The zeolite may be an H-ZSM-5 catalyst from Zeolyst International for cracking waxes and aromatizing light olefins. The ZSM-5 zeolites were originally developed by Mobil Oil Company in the 1970s to crack heavy oils and convert methanol to aromatic gasoline constituents. The H-ZSM-5 catalyst has demonstrated a reduction in waxy FT hydrocarbons from about 20 wt. % to about 5 wt. %

Exemplary Hydrogenation Reactor

In another downstream processing step, dewaxed liquid fuels from the cracking operations may be sent through a fixed bed of palladium hydrogenation catalyst to saturate olefinic sites and stabilize the liquid fuel products. A hydrogenation catalyst that contains about 0.5% palladium on alumina (e.g., Aldrich No. 520675) may be used in the hydrogenation reactor. Tests from current operations indicate the partial pressure of residual hydrogen processed gas (around 12 vol. %) is sufficient to cap-off and stabilize reactive olefin sites.

Analysis of FT Product Distributions

GC/MS analysis of FT products (a.k.a. synfuels) from an embodiment of the BTL system show branched hydrocarbons are the major constituents of the syngasoline fraction, along with some methyl- and ethyl-substituted monocyclic aromatics. The raw syngasoline fraction has a projected relatively high octane rating. Like most ultra-low sulfur FT liquid fuels, straight-chain hydrocarbons are the major constituents of CPC's synthetic diesel (syndiesel) product. Our syndiesel, however, also contains small amounts (e.g., less than 15 wt. %) of methyl- and ethyl-monocyclic aromatics from the H-ZSM-5 cracking operations. This results in a FT fuel with a lower cloud point and fewer anticipated problems with elastomeric seals than more typical, highly paraffinic F-T fuels.

Estimated Product Yields:

A bench-top continuous-flow system has demonstrated over 15% conversion of CO in a two-stage simulation, with half the CO consumption for FT production of liquid fuels, and the other half used to generate more hydrogen and eliminate waste water via the WGS reaction. Assuming 70% of the hydrocarbon products are the gasoline and diesel fuel fractions, the projected yield of the system is around 42 gallons of synfuels per ton of dry biomass. This quantity of liquid hydrocarbon fuel contains the energy of about 68 gallons of ethanol.

The CO consumption by the WGS reaction may be reduced by employing a hydrogen-selective to recover and recycle hydrogen from the system off-gas and increase the projected yields of liquid fuels by 15% to a projected 48 gallons of hydrocarbons/ton of dry biomass (equivalent to 78 gallons of ethanol per ton).

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the catalyst" includes reference to one or more catalysts and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. An apparatus for converting a carbon-containing feedstock into a fluid transportation fuel, the apparatus comprising:

a producer gas reactor operable to convert the carbon-containing feedstock into a producer gas comprising $H_2$, CO, $CO_2$, and $N_2$; and a Fischer-Tropsch reactor fluidly coupled to the producer gas reactor, wherein the Fischer-Tropsch reactor is operable to receive the producer gas comprising $H_2$, CO, $CO_2$, and $N_2$ and to convert a portion of the producer gas into a combination of Fischer-Tropsch (F-T) products, the F-T products including the fluid transportation fuel;

a cracking reactor fluidly coupled to the Fischer-Tropsch reactor, wherein the cracking reactor is operable to catalytically crack a portion of the F-T products to produce additional amounts of the fluid transportation fuel; and a hydrogenation reactor fluidly coupled to the cracking reactor, wherein the hydrogenation reactor is operable to hydrogenate a portion of the F-T products to produce additional amounts of the fluid transportation fuel.

2. The apparatus of claim 1, wherein the producer gas reactor is a biomass gasification reactor operable to convert biomass and air into the producer gas.

3. The apparatus of claim 2, wherein the biomass is selected from the group consisting of woody biomass, non-woody biomass, a cellulosic product, cardboard, fiber board, paper, plastic, and a food stuff.

4. The apparatus of claim 1, wherein the Fischer-Tropsch reactor comprises a cylindrical tube filled with a Fischer-Tropsch catalyst, wherein the tube has a diameter ranging from about 2 inches to about 3.5 inches.

5. The apparatus of claim 1, wherein the Fischer-Tropsch reactor comprises a Fischer-Tropsch catalyst comprising iron.

6. The apparatus of claim 1, wherein the Fischer-Tropsch reactor comprises as Fischer-Tropsch catalyst operable to catalyze a water-gas-shift reaction between $H_2O$ and CO to produce $H_2$ and $CO_2$.

7. The apparatus of claim 1, wherein the cracking reactor comprises a cracking catalyst comprising a zeolite that can catalytically crack waxes and aromatize light olefins.

8. The apparatus of claim 7, wherein the zeolite comprises a ZSM-5 zeolite.

9. The apparatus of claim 1, wherein the hydrogenation reactor comprises a hydrogenation catalyst comprising palladium.

10. The apparatus of claim 9, wherein the hydrogenation catalyst comprises palladium on alumina.

* * * * *